(12) United States Patent
Seonwoo

(10) Patent No.: US 10,202,502 B2
(45) Date of Patent: Feb. 12, 2019

(54) METHOD FOR PRODUCING ANTIMICROBIAL POLYESTER FIBER YARN CONTAINING VOLCANIC ASH

(71) Applicant: Kwon Seonwoo, Iksan (KR)

(72) Inventor: Kwon Seonwoo, Iksan (KR)

(*) Notice: Subject to any disclaimer, the term of this patent is extended or adjusted under 35 U.S.C. 154(b) by 189 days.

(21) Appl. No.: 15/333,618

(22) Filed: Oct. 25, 2016

(65) Prior Publication Data
US 2017/0145192 A1    May 25, 2017

(30) Foreign Application Priority Data
Nov. 24, 2015 (KR) .......................... 10-2015-0164704

(51) Int. Cl.
| | | |
|---|---|---|
| *C08K 11/00* | (2006.01) | |
| *D02G 3/04* | (2006.01) | |
| *D02G 3/16* | (2006.01) | |
| *B29C 47/00* | (2006.01) | |
| *B29B 9/12* | (2006.01) | |
| *B29B 7/00* | (2006.01) | |
| *A01N 59/00* | (2006.01) | |
| *B29B 7/88* | (2006.01) | |
| *D01F 1/10* | (2006.01) | |
| *D01F 6/62* | (2006.01) | |
| *B29K 67/00* | (2006.01) | |

(Continued)

(52) U.S. Cl.
CPC .............. *C08K 11/00* (2013.01); *A01N 59/00* (2013.01); *B29B 7/005* (2013.01); *B29B 7/885* (2013.01); *B29B 9/12* (2013.01); *B29C 47/0014* (2013.01); *D01F 1/103* (2013.01); *D01F 6/62* (2013.01); *D02G 3/045* (2013.01); *D02G 3/16* (2013.01); *B29B 9/06* (2013.01); *B29K 2067/00* (2013.01); *B29K 2105/162* (2013.01); *B29K 2509/00* (2013.01); *B29K 2995/0037* (2013.01); *B29L 2031/731* (2013.01); *C08K 3/015* (2018.01); *C08K 2201/011* (2013.01)

(58) Field of Classification Search
None
See application file for complete search history.

(56) References Cited

U.S. PATENT DOCUMENTS

2004/0137227 A1* 7/2004 Masuda .................... D01F 6/92
428/395

FOREIGN PATENT DOCUMENTS

| KR | 10-2014-0100609 B1 | 4/2015 |
|---|---|---|
| KR | 10-2014-0024572 A | 10/2015 |
| KR | 1020150102549 | * 10/2015 |

* cited by examiner

*Primary Examiner* — Nathan T Leong
(74) *Attorney, Agent, or Firm* — Patent Office of Dr. Chung Park

(57) ABSTRACT

The present invention relates to a method for producing an antimicrobial polyester fiber yarn containing volcanic ash, the method comprising the steps of: crushing and heating volcanic ash, and allowing the heated volcanic ash to collide under an air stream in an air classifier mill system to obtain volcanic ash powder; subjecting the volcanic ash powder to nano-milling to obtain nano-sized volcanic ash particles; disintegrating the volcanic ash particles to prepare nano volcanic ash; mixing the prepared nano volcanic ash with polyester for fiber use at a weight ratio of 10:90-30:70, followed by melt extrusion, thereby preparing a highly dispersed volcanic ash master batch; and mixing the volcanic ash master batch with polyester for fiber use at a weight ratio of 4:96-8:92, followed by spinning to produce an antimicrobial polyester fiber yarn.

4 Claims, 1 Drawing Sheet

(51) Int. Cl.
*B29K 105/16* (2006.01)
*B29K 509/00* (2006.01)
*B29L 31/00* (2006.01)
*B29B 9/06* (2006.01)
*C08K 3/015* (2018.01)

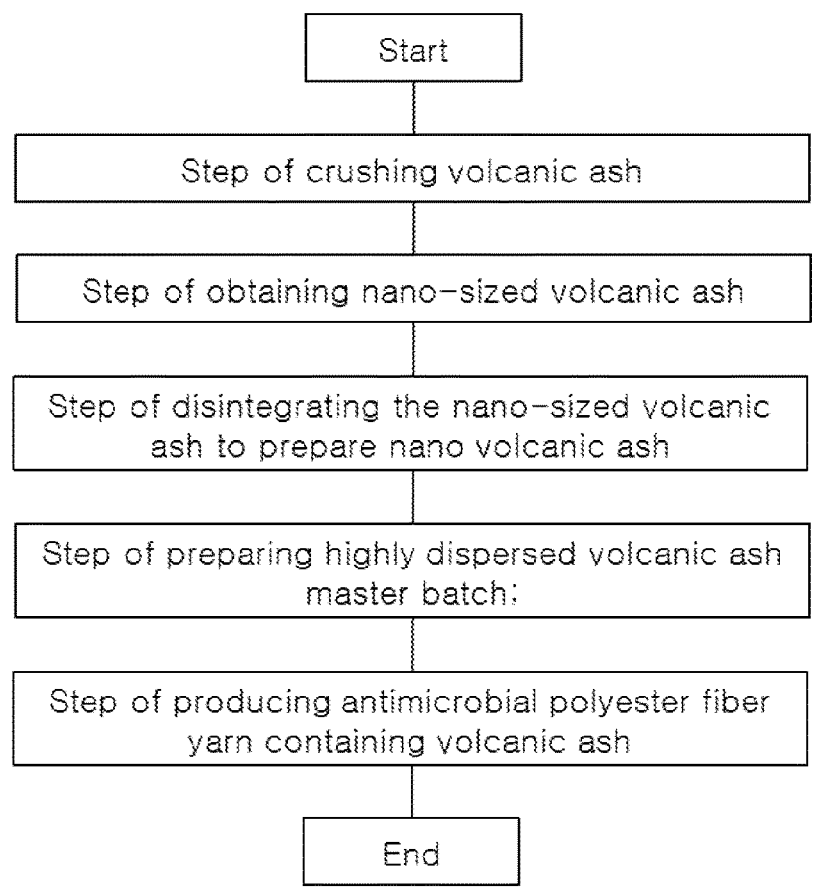

10,202,502 B2

METHOD FOR PRODUCING ANTIMICROBIAL POLYESTER FIBER YARN CONTAINING VOLCANIC ASH

CROSS-REFERENCE TO RELATED APPLICATIONS

This U.S. non-provisional patent application claims priority under 35 U.S.C. § 119 of Korean Patent Application No. 10-2015-0164704 filed on Nov. 24, 2015, the entire contents of which are hereby incorporated by reference.

BACKGROUND OF THE INVENTION

Field of the Invention

The present invention relates to a method for producing an antimicrobial yarn comprising a mixture of the mineral volcanic ash and the fibrous material polyester, and more particularly to a method for producing an antimicrobial polyester fiber yarn containing volcanic ash, in which the antimicrobial polyester fiber yarn is produced by preparing a volcanic ash master batch, mixing the master batch with a polyester chip, and spinning the mixture, and exhibits the antimicrobial, deodorizing and far infrared-emitting functions of volcanic ash in an excellent way and, at the same time, is environmentally friendly.

Description of the Prior Art

The development and use of chemical fibers such as polyester, nylon or acrylic fibers has increased rapidly. In recent years, chemical fibers having various functions have been developed and widely used in various applications, including various clothing materials and industrial materials.

In the comparison of natural fibers with chemical fibers, cotton fiber that is most commonly used as a natural fiber shows the characteristics of environmentally friendly fiber with excellent moisture absorption, warm keeping, soft tactile sensation, air permeability and antistatic properties when being produced into a product, but has problems, including poor dimensional stability, low mechanical strength, occurrence of contamination and discoloration, low color fastness to washing, etc.

On the other hand, polyester fiber that is a typical chemical fiber has excellent mechanical strength, elasticity and tension, and excellent durability properties, including weather resistance and washing fastness, but has problems in that it is not soft, is dry, and has poor antistatic properties, indicating that it is not environmentally friendly.

As described above, cotton fiber, which is a natural fiber, and polyester fiber which is a chemical fiber, each has advantages and disadvantages, and products employing the characteristics of each fiber have been produced.

The living conditions of modern people are as follows: (1) modern people lead a busy life; (2) they emphasize a fast and convenient way; (3) they emphasize an economic and stylish design; and (4) they prefer products having various functionalities.

In the present state, it is difficult to further develop cotton fiber into products that satisfy such conditions. For this reason, there is a great need to develop products which are made of chemical materials and which satisfy not only the above-described four conditions, but also various functionalities which have recently been required. As polyester fiber products, products, which have various kinds of yarns and emphasize various functionalities, can be, developed, but have a problem in that they are hardly recognized as environmentally friendly materials, which is the, biggest problem of chemical fibers.

The present invention has been made in order to solve this problem of chemical fibers, and is intended to provide a method for producing an antimicrobial yarn, in which volcanic ash containing a variety of functional inorganic materials, including silicon dioxide, aluminum oxide, iron, oxide, titanium dioxide, sodium, oxide, etc., is incorporated by a novel technical method during chemical fiber spinning.

SUMMARY OF THE INVENTION

The present invention has been made in order to solve the above-described problems, and it is an object of the present invention to provide a method in which volcanic ash is incorporated into polyester and spun to produce polyester fiber, so that the characteristic properties of the natural material volcanic ash in the polyester fiber are sufficiently exhibited while the properties of the polyester fiber are also maintained.

To achieve the above object, the present invention provides a method for producing an antimicrobial polyester fiber yarn containing volcanic ash, the method comprising the steps of: crushing volcanic ash in two steps, heating the crushed volcanic ash, and allowing the heated volcanic ash to collide under an air stream in an air classifier mill system to obtain volcanic ash powder; subjecting the volcanic ash powder to nano-milling to obtain nano-sized volcanic ash particles; disintegrating the volcanic ash particles to prepare nano volcanic ash; mixing the prepared nano volcanic ash with polyester for fiber use at a weight ratio of 10:90-30:70, followed by melt extrusion to prepare a volcanic ash master batch; and mixing the volcanic ash master batch with polyester for fiber use at a weight ratio of 4:96-8:92, followed by spinning to produce an antimicrobial polyester fiber yarn.

BRIEF DESCRIPTION OF THE DRAWINGS

FIG. 1 is a flowchart showing a method for producing an antimicrobial polyester fiber yarn containing volcanic ash according to a preferred embodiment of the present invention.

DETAILED DESCRIPTION OF THE INVENTION

The present invention is directed to a method for producing an antimicrobial polyester fiber yarn containing volcanic ash, the method comprising: crushing volcanic ash; milling the crushed volcanic ash to obtain nano-sized volcanic ash; preparing a volcanic ash master batch using the nano-sized volcanic ash; mixing the prepared volcanic ash master batch with polyester for fiber use; and spinning the mixture.

Rock fragments which are discharged in a broken state due to either an impact caused by volcanic activity or volcanic gas erosion are referred to as pyroclastic material. Among volcanic lava fragments, deposits of small grains having a size of about 0.25-4 mm are referred to as volcanic ash.

In the present invention, Jeju volcanic ash collected by taking a portion ranging from the surface layer to a depth of 50 cm or more in a non-contaminated area in Gujwa-eup, Jeju-do, Korea, may be used.

Herein, the non-contaminated area is an area in which energy beneficial to organisms is emitted and which shows 0 Gauss when measuring quantum energy, emitted from the land surface, by a Gauss meter. This area is a place suitable for growth of humans, animals and plants and is characterized in that energy is formed in the form of a circle in this space. Namely, the inside of the space of the circle is maintained at a magnetic field of 0, and has a land surface temperature which is 4° C. higher than that of the outside, has no moisture, and moss and fungi in the surrounding portion are killed and exterminated, indicating that the inside is clean and clear.

The Jeju volcanic ash is an inorganic mineral (bentonite) containing, as main components, inorganic materials such as $SiO_2$, $Al_2O_3$, $Fe_2O_3$, $TiO_2$, $Na_2O_3$ and the like, is in a powder form, and is easily powdered into smaller particles even by light impact.

In addition, the Jeju volcanic ash is lighter than general sand, and has higher water absorption rate and porosity.

The method of the present invention is started from a step of crushing the Jeju volcanic ash. The Jeju volcanic ash is primarily crushed using a jaw crusher and secondarily crushed using a hammer crusher, and the crushed volcanic ash having a size of less than 2 mm is heated in a ceramic electric furnace at a temperature of 300 to 350° C. for 120-150 minutes. The heated volcanic ash is dried, and then cooled to room temperature. Next, the cooled volcanic ash is further crushed in an air classifier mill system by forming an air stream in the mill at 2500-3500 rpm to allow the volcanic ash particles to collide with one, another. The resulting crushed. volcanic ash powder has a size of 500-1000 mesh, When the volcanic ash is heated at the, above-described temperature, various organic impurities and pore water are removed from the volcanic ash while the characteristic properties of the volcanic ash are maintained. In addition, the porosity of the volcanic ash increases to reduce the specific gravity of the volcanic ash. Through air milling, the volcanic ash is changed from an irregular particle shape to a shape approaching a sphere. For this reason, the difference in specific gravity of the volcanic ash from that of polyester which is used in preparation of a master batch as described below and mixing and spinning with polyester as described below is reduced, and the volcanic ash particles have a spherical shape and a uniform size, indicating that the miscibility and dispersibility of the volcanic ash are improved.

Next, a step of subjecting the crushed volcanic ash to nano-milling is performed. Because the crushed volcanic ash includes micrometer-sized volcanic ash particles, the crushed volcanic ash is vibration-milled with water in a vibration mill by use of 0.5-2.0-mm-diameter balls made of alumina or silica which is a component similar to that of the volcanic ash, and the balls are separated using a filter.

After separation of the balls, 10-30 parts by weight of calcium hydroxide, is added to 100 parts by weight of a solution obtained by the vibration milling, followed by uniform stirring of the solution. Then, the stirred solution was allowed to stand for 12-24 hours, followed by centrifugation. Then, large, precipitated particles are discarded, and only the remaining thin solution free of micrometer-sized particles is recovered, thereby obtaining a suspension containing nano-milled volcanic ash particles having a size of 200-900 nm.

Herein, the vibration milling may be performed at a speed of 300-900 cycles/minute for 12-36 hours, and the centrifugation may be performed at 3,000-9,000 rpm for 10-30 minutes, If the conditions of the vibration milling and centrifugation are lower than the lower limits of the above-described ranges, it will be difficult to obtain nanometer-sized particles, and if the, conditions are higher than the upper limits, aggregation between the particles will occur, and economic efficiency will decrease.

When such vibration milling speed and time and centrifugation speed and time are, controlled as described above, nanometer-sized particles having a narrow particle size distribution will be obtained from micrometer-sized volcanic ash in a simple and easy manner.

In addition, when calcium hydroxide is added, it is ionized in water and reacts with the inorganic oxides of the volcanic ash to promote the generation of negative charges in the volcanic ash to thereby cause the particles to repel from one another, thereby preventing the particles from aggregating with one another.

After the nano-milling step, a step of drying and disintegrating the suspension containing the volcanic ash particles to prepare nano volcanic ash is performed.

For the drying, a conventional method may be used without particular limitation.

When the, dried nanometer-sized volcanic ash powder is treated using a conventional ultrasonic homogenizer for a predetermined time or is treated for a predetermined time by use of a jet-mill apparatus that blows powder to a high-temperature and high-speed fluid at 70 to 120° C., the nanometer-sized volcanic ash is rapidly disintegrated.

When the jet-mill apparatus is used, ultrahigh-pressure counter jet streams of a high-temperature fluid containing the volcanic ash powder are, preferably allowed to collide with each other. When the counter jet streams are allowed to collide with each other for a predetermined time at a stream radius of 0.1 mm, a jet stream rate of 600 m/sec and a jet stream flow rate of 15 l/min through a nozzle, the nanometer-sized volcanic ash powder aggregates can be disintegrated into nanometer-sized volcanic ash particles within a short time while water in the pores of the volcanic particles is removed.

Because the jet mill disintegration is carried out at high temperature, the dry state becomes good, water and impurities are removed, pores develop to reduce the apparent specific gravity, and a complete particle size distribution can be achieved. This can solve problems in that the volcanic ash particles milled into nanoparticles are not completely dispersed and in that some of the particles adhere to one another so that the particles cannot be uniformly mixed in the preparation of a master batch to thereby increase the pressure in spinning.

Next, a step of preparing a volcanic ash master batch using the prepared nano volcanic ash is performed.

Preparation of the volcanic ash master batch can be performed by a high-dispersion preparation method (which is a preparation method performed for a long time) so that the nano volcanic ash can be uniformly dispersed. When the high-dispersion preparation method is used, mixing between the volcanic ash and polyester can be easily achieved, and the volcanic ash can be uniformly distributed in polyester.

The, high-dispersion preparation method may comprise the steps of: dispersing the nano volcanic ash; crushing the nano volcanic ash; and mixing the nano volcanic ash with polyester.

Specifically, using a tumbler mixer, 10-30 parts by weight of phosphoric acid ester such as triethyl phosphate or tributyl phosphate, which serves as a first dispersing agent, is dry mixed with 100 parts by weight of volcanic ash obtained by passing the prepared nano volcanic ash through a 300-350 mesh sieve so that it is attached to the surface of the volcanic ash. Then, 70-90 parts by weight of 2,2'-bis(4-hydroxyphenyl)propane or hydroquinone, which serves as a second dispersing agent, is added thereto and mixed, and the mixture is softened at a temperature of 100 to 150° C., dispersed for 50-70 minutes, and cooled.

When the dispersion is performed at the above-described temperature, the first dispersing agent attached to the surface of volcanic ash is fluidized by glycol serving as the second dispersing agent, and is adsorbed uniformly onto the surface, and pores of the volcanic ash, and thus the first dispersing agent and the second dispersing agent exhibit dispersing performance, even at a high temperature, for melting of polyester.

The dispersed nano volcanic ash can be crushed into flakes by use of a crusher that is generally used. In this case, agglomeration in the dispersing process can be solved so that mixing in the next step can be facilitated.

For mixing with polyester, the flaked nano volcanic ash and polyester are mixed at a weight ratio of 10:90-30:70 in a super mixer and stirred at a temperature of 100 to 120° C. for 15-20 hours.

If the mixing ratio between the, nano volcanic ash and the polyester is out of the above-described range, the properties of the volcanic ash will not be exhibited, or dispersion of the volcanic ash will be insufficient due to the excessive amount of the volcanic ash so as to cause yarn breakage in the production of polyester fiber or to reduce the fiber strength.

The resulting mixture is extruded through an extruder at a temperature of 260 to 290° C. at which polyester can be melted. The extruded material is cooled and pelletized, thereby preparing a volcanic ash master batch. The prepared master batch pellets have a length of 3-3.5 mm and a diameter of 2-3 mm.

Meanwhile, in addition to polyester as a base for the master batch, polyethylene or polyamide may also be used at a controlled extrusion temperature.

Next, a step of producing a volcanic ash-containing antimicrobial yarn using the volcanic ash master batch is performed.

The, method for producing the volcanic ash-containing antimicrobial yarn according to the present invention is preferably performed using a general method under the following conditions.

The, volcanic ash master batch and polyester for fiber use are mixed with each other at a weight ratio of 4:96-8:92 and extruded. Herein, the mixture may be passed through 100-120 mesh sand in a spinning pack and passed through 400-420 mesh filter, and then spun through a circular cross-sectional nozzle. The spinning may be performed at an internal pressure, of 110-130 kg/cm$^2$ and an external pressure of 110-130 kg/cm$^2$. After the spinning, the spun yarn may be cooled in a cooling chamber at a temperature of 17 to 23° C. and wound, thereby producing an antimicrobial yarn containing volcanic ash.

According to the present invention, after spinning through the circular cross-sectional nozzle, a filament yarn such as SDY (Spin Draw Yarn) or DTY (Draw Textured Yarn) is produced as a circular cross-sectional yarn.

SDY is a draw yarn produced by a process in which spinning and drawing are performed at the same time. It is produced by performing drawing at a predetermined level using the speed difference between heating rollers in a spinning process. Specifically, it is produced by performing drawing at a ratio of 60-65% through rollers. More specifically, it is a fiber obtained by heat setting at a temperature of 85 to 90° C. in a first roller and a temperature of 115 to 120° C. in a second roller, followed by winding at a rate of 5000-5500 m/min. The obtained SDY is used alone to produce general textiles and is referred to as a filament yarn.

DTY is a fiber produced by a process in which drawing and false twisting are performed at the same time as spinning. Specifically, it is a fiber obtained by performing drawing in the same manner as the production of SDY, and then performing false, twisting at a temperature of 185 to 195° C., followed by winding at a rate of 3200-3300 m/min. The obtained DTY is used for knitting or blend weaving with other fibers and is referred to as a Poy yarn.

In addition, according to the present invention, a shaped yarn or a sheath/core yarn may be produced using another nozzle as a substitute for the circular cross-sectional nozzle.

The shaped yarn according to the present invention is produced using a nozzle having a cross-sectional shape such as a triangular, star or cross shape. Specifically, it is produced in the, same manner as the above-described yarn production method by use of a shaped nozzle as a substitute for the circular cross-sectional nozzle, and has functionalities such as warm-keeping properties, quick sweat absorption and drying properties, draft properties, silk-like gloss, silk-like sensation, and the like.

The sheath/core yarn according to the present invention is produced using a nozzle having a core portion and a sheath portion in the cross section, in which polyester alone is passed through the core portion, and a mixture obtained by mixing the volcanic ash master batch and polyester for fiber use at a weight ratio of 4:96-8:92 is passed through the sheath portion. It is a yarn produced in the same manner as the above-described yarn production method. In the case of the sheath/core yarn, the effects of the present invention by volcanic ash are improved, and the strength of the yarn is improved.

Hereinafter, the results of evaluating a circular cross-sectional polyester yarn, produced according to the above-described method and containing 1.2 wt % of volcanic ash, woven/knitted fabrics produced using the polyester yarn, will be described.

Table 1 below shows the results of an antimicrobial activity test conducted by the FITI Testing & Research Institute (Korea) for a fabric composed of an antimicrobial polyester fiber yarn containing volcanic ash according to the present invention.

TABLE 1

| Antimicrobial activity (KS K 0693: 2011) | | | |
|---|---|---|---|
| | | Blank | #3 |
| Strain 1 | Initial number of bacterial cells (cells/ml) | $2.1 \times 10^4$ | $2.1 \times 10^4$ |
| | After 18 hours (cells/ml) | $2.0 \times 10^6$ | $4.6 \times 10^2$ |
| | Bacteria reduction rate (%) | — | 99.9 |
| Strain 2 | Initial number of bacterial cells (cells/ml) | $2.1 \times 10^4$ | $2.1 \times 10^4$ |
| | After 18 hours (cells/ml) | $1.3 \times 10^7$ | $8.3 \times 10^3$ |
| | Bacteria reduction rate (%) | — | 99.9 |

Note)
Standard fabric: cotton;
test strains used: strain 1 - *Staphylococcus aureus* ATCC 6538; strain 2: *Klebsiella pneumoniae* ATCC 4352.

As can be, seen in Table 1 above, the antimicrobial activity of a woven fabric composed of a 150D/48F antimicrobial polyester fiber yarn containing volcanic ash was measured according to the method of KS K 0693: 2011, and as a result, the bacteria reduction rate after 18 hours was 99.9%, indicating that the fabric has excellent antimicrobial activity.

Table 2 below shows the results of evaluating the deodorization rate of a knitted fabric composed of an antimicrobial polyester fiber yarn containing volcanic ash according to the present invention.

Specifically, Table 2 shows the results of a test conducted by the, FITI Testing & Research Institute by measuring the deodorization rate of a knitted fabric composed of a 150D/48F antimicrobial polyester fiber yarn containing volcanic ash.

TABLE 2

| Test item<br>Deodorization rate (%): gas detection tube method<br>Test time | Test results<br>Sample 1 |
|---|---|
| 30 min | 54 |
| 60 min | 60 |
| 90 min | 66 |
| 120 min | 70 |

As can be, seen in Table 2 above, the deodorization rate after 120 minutes was 70%, suggesting that the knitted fabric has excellent deodorization ability.

Table 3 below shows the results of a fax-infrared emissivity test for a fabric composed of an antimicrobial polyester fiber yarn containing volcanic ash. Specifically, Table 3 shows the results of emissivity and radiated energy tests conducted by the Korea Conformity Laboratories.

TABLE 3

| | (test method: KCL-FIR-1025: 2011) | | | |
|---|---|---|---|---|
| Test items | Unit | Test method | Test results | Test environment |
| Far-infrared emissivity (measurement temperature: 40° C.; measurement wavelength: 5-20 μm) | — | (1) | 0.881 | (22.3 ± 0.1° C.) (24.3 ± 0.3) % R.H. |
| Far-infrared radiation energy (measurement temperature: 40° C.; measurement wavelength: 5-20 μm) | $W/m^2$ | (1) | 3.56 × $10^2$ | (22.3 ± 0.1° C.) (24.3 ± 0.3) % R.H. |

The test results are the results obtained by measurement in comparison with a black body by use of an FT-IR spectrometer.

As can be seen from the results in Table 3 above, the fabric emits far-infrared rays. Thus, the fabric can give a warm feeling even at room temperature when being worn.

Table 4 below shows the results of a mechanical strength test conducted by the FITI Testing & Research Institute (Korea) for an antimicrobial polyester fiber yarn containing volcanic ash according to the present invention.

TABLE 4

| #1 | #2 |
|---|---|
| 01. Specific strength (KS K 0412: 2010, C.R.E.): cN/denier (gf/denier) | |
| 3.93 (4.01) | 4.26 (4.34) |
| 02. Tensile elongation (KS K 0412: 2010, C.K.E.): % | |
| 20.0 | 25.6 |

Note)
According to the client's request, gf/denier was described in parentheses.
A coefficient for converting gf/denier to cN/denier is 0.980 665.

As can be seen in Table 4 above, the specific strength and tensile elongation of the antimicrobial polyester fiber yarn containing volcanic ash were similar to those of a general polyester yarn, suggesting that the antimicrobial polyester fiber yarn has excellent mechanical strength.

Table 5 below shows the results of testing the washing fastness of a fabric composed of an antimicrobial polyester fiber yarn containing volcanic ash according to the present invention.

TABLE 5

| 01. washing fastness (KS K ISO 105 C06: 2014, A2S; washing temperature (40 ± 2) ° C.; washing time: 30 min; 0.4% ECE standard detergent; 0.1% sodium perborate; the number of steel balls: 10): grade | |
|---|---|
| | #3 |
| Discoloration/fading | 4-5 |
| Contamination | |
| cotton | 4-5 |
| polyester | 4-5 |

As can be seen in Table 5 above, the washing fastness of the fabric composed of the antimicrobial polyester fiber yarn containing volcanic ash was equal to that of a cotton or polyester fabric.

Particularly, according to the present invention, volcanic ash that is used in the present invention is in the form of nano-sized powder, is easily dispersed, and has a low apparent specific gravity so as to have improved miscibility with polyester so that it can be easily spun through a nozzle without excessively increasing the pack pressure. In addition, the friction strength of the surface of the antimicrobial polyester fiber yarn is reduced by volcanic ash, and the antimicrobial polyester fiber yarn is easily processed due to the moisture-absorbing property of volcanic ash, and volcanic ash is uniformly dispersed in the polyester fiber yarn, so that the characteristic properties of the volcanic ash will be exhibited even when the content of the volcanic ash in the yarn is low. Additionally, the yarn is easily dyed and, at the same time, has a high washing fastness and a high stability against contamination.

Because the antimicrobial polyester fiber yarn containing volcanic ash according to the present invention has the above-described characteristics, it can be used in cloth products, including functional underwear, adult outdoor wear, infant underwear, and sports socks, bedding products, including bedclothes, mats and bed sheets, sofas, cushions, diapers, dressings, and general clothes, as well as industrial materials such as various nonwoven fabrics, packaging materials and automotive, filters, which can be produced using the antimicrobial polyester fiber yarn.

As described above, products produced using the antimicrobial fiber yarn comprising a mixture of volcanic ash and polyester according to the present invention contains volcanic ash, and thus are environmentally friendly, and, at the same time, can have various functionalities, including antimicrobial, deodorizing and far-infrared-emitting properties.

In addition, products produced using polyester fiber alone has a moisture regain of only 0.4%, and thus have a low ability to absorb moisture, and become hard, indicating that it is difficult to improve the moisture-absorbing ability, warm-keeping ability and air permeability of the products. However, products produced using the antimicrobial fiber yarn comprising a mixture of volcanic ash and polyester according to the present invention contains a porous material (volcanic ash) that improves the moisture-absorbing ability, moisture-retaining ability and softness of the products, and the porous material contained can also improve fastness and solve dyeing problems such as stains. In addition, the porous material contains mineral components that can overcome problems, including skin troubles occurring upon contact with the skin, and dry skin.

Furthermore, the volcanic ash is uniformly dispersed as nano-sized particles without acting as an impurity, and. thus can improve the washing fastness of the fiber yarn without reducing the mechanical properties of the fiber yarn.

In addition, the polyester fiber yarn according to the present invention emits far-infrared rays that provide warming at room temperature and an environmentally friendly atmosphere beneficial to the human body.

What is claimed is:

1. A method for producing an antimicrobial polyester fiber yarn containing volcanic ash, the method comprising the steps of:
    crushing volcanic ash using a first crusher;
    using a second crusher, crushing the volcanic ash crushed by the first crusher;
    heating the volcanic ash crushed by the second crusher and causing the heated volcanic ash to collide under an air stream in an air classifier mill system to obtain volcanic ash powder;
    subjecting the volcanic ash powder to nano-milling to obtain nano-sized volcanic ash particles;
    disintegrating the nano-sized volcanic ash particles to prepare nano volcanic ash;
    preparing a dispersed volcanic ash master batch using the nano volcanic ash; and
    mixing the dispersed volcanic ash master batch with polyester for fiber use at a weight ratio of 4:96-8:92, followed by spinning to produce an antimicrobial polyester fiber yarn,
    wherein the step of preparing a dispersed volcanic ash master batch comprises: (1) dry-mixing 10-30 parts by weight of triethyl phosphate or tributyl phosphate as a first dispersing agent with 100 parts by weight of the nano volcanic ash; (2) adding 70-90 parts by weight of 2,2'-bis(4-hydroxyphenyl) propane as a second dispersing agent to the mixture generated in step (1); (3) dispersing the mixture generated in step (2) to generate dispersed nano volcanic ash; (4) crushing the dispersed nano volcanic ash into nano volcanic ash flakes; and (5) mixing the nano volcanic ash flakes with polyester, followed by melt exclusion.

2. The method of claim 1, wherein the step of heating the volcanic ash is performed at a temperature of 300 to 350° C. for 120-150 minutes.

3. The method of claim 1, wherein the step of subjecting the volcanic ash powder to nano-milling to obtain nano-sized volcanic ash particles comprises: subjecting the volcanic ash powder to vibration milling with water; adding 10-30 parts by weight of calcium hydroxide to 100 parts by weight of a solution obtained by the vibration milling; centrifuging the solution containing the calcium hydroxide; discarding large precipitated particles after the centrifugation; and recovering only a thin suspension containing nano-sized volcanic ash particles after the centrifugation.

4. The method of claim 1, wherein the step of disintegrating the nano-sized volcanic ash particles to prepare the nano volcanic ash comprises: drying the nano-sized volcanic ash particles; and disintegrating the dried nano-sized volcanic ash particles by use of a jet-mill apparatus that blows powder to a fluid having a high temperature of 70 to 120° C.

* * * * *